(12) United States Patent
Boy et al.

(10) Patent No.: US 9,833,454 B2
(45) Date of Patent: Dec. 5, 2017

(54) DIFLUOROMETHOXY COMPOUND WITH LOW BIOACTIVATION POTENTIAL FOR THE REDUCTION OF BETA-AMYLOID PRODUCTION

(71) Applicant: BRISTOL-MYERS SQUIBB COMPANY, Princeton, NJ (US)

(72) Inventors: Kenneth M. Boy, Durham, CT (US); Stephen E. Mercer, Middletown, CT (US); Richard E. Olson, Orange, CT (US); Xiaoliang Zhou, Guilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 15/300,602

(22) PCT Filed: Apr. 1, 2015

(86) PCT No.: PCT/US2015/023779
§ 371 (c)(1),
(2) Date: Sep. 29, 2016

(87) PCT Pub. No.: WO2015/153709
PCT Pub. Date: Oct. 8, 2015

(65) Prior Publication Data
US 2017/0182050 A1    Jun. 29, 2017

Related U.S. Application Data

(60) Provisional application No. 61/973,917, filed on Apr. 2, 2014.

(51) Int. Cl.
| | | |
|---|---|---|
| *C07D 239/70* | (2006.01) | |
| *C07D 491/00* | (2006.01) | |
| *C07D 471/00* | (2006.01) | |
| *C07D 413/00* | (2006.01) | |
| *A61K 31/517* | (2006.01) | |
| *C07D 403/12* | (2006.01) | |

(52) U.S. Cl.
CPC .......... *A61K 31/517* (2013.01); *C07D 403/12* (2013.01); *A61K 2121/00* (2013.01)

(58) Field of Classification Search
CPC .. C07D 239/70; C07D 491/00; C07D 495/00; C07D 471/00; C07D 413/00; A61K 31/517
USPC ............... 514/258.1; 544/253, 278, 279, 117
See application file for complete search history.

(56) References Cited

U.S. PATENT DOCUMENTS

| | | | |
|---|---|---|---|
| 8,486,952 B2 * | 7/2013 | Boy | ..................... A61K 31/517 514/210.21 |
| 8,637,523 B2 | 1/2014 | Boy et al. | |
| 8,637,525 B2 | 1/2014 | Boy et al. | |

* cited by examiner

*Primary Examiner* — Niloofar Rahmani
(74) *Attorney, Agent, or Firm* — John F. Levis

(57) ABSTRACT

The compound N2-(3-(difluoromethoxy)-4-(3-methyl-1H-1,2,4-triazol-1-yl)phenyl)-7-(4-fluorophenyl)-N4,5,5-trimethyl-6,7-dihydro-5H-cyclopenta[d]pyrimidine-2,4-diamine: [PLEASE INSERT CHEMICAL STRUCTURE HERE] reduces -amyloid peptide (A 42) production and has low potential for bioactivation, and may be useful in the treatment of Alzheimer's Disease and other conditions affected by -amyloid peptide (A 42) production.

7 Claims, No Drawings

DIFLUOROMETHOXY COMPOUND WITH LOW BIOACTIVATION POTENTIAL FOR THE REDUCTION OF BETA-AMYLOID PRODUCTION

CROSS REFERENCE TO RELATED APPLICATION

This application claims the benefit of U.S. Ser. No. 61/973,917 filed Apr. 2, 2014, the entire contents of which is herein incorporated in its entirety.

FIELD OF THE INVENTION

The present invention relates to a new difluoromethoxy compound with low bioactivation potential which is a modulator of β-amyloid peptide (Aβ) production, as well as to methods of treating Alzheimer's Disease (AD) and other conditions related to β-amyloid production using this compound. The invention further relates to pharmaceutical compositions comprising this compound.

BACKGROUND OF THE INVENTION

Alzheimer's disease (AD) is a progressive neurodegenerative disease which begins with memory loss and progresses to include severe cognitive impairment, altered behavior, and decreased motor function (Grundman, M. et al., Arch Neurol. (2004) 61: 59-66; Walsh, D. M. et al., Neuron (2004) 44: 181-193). It is the most common form of dementia and represents the third leading cause of death after cardiovascular disorders and cancer. The cost of AD is enormous and includes the suffering of the patients and families and the lost productivity of patients and caregivers (Wimo A, Prince M: World Alzheimer Report 2010: the Global Economic Impact of Dementia). No treatment that effectively prevents AD or reverses the clinical symptoms and underlying pathophysiology is currently available (Karran E, Mercken M, De Strooper B, "The amyloid cascade hypothesis for Alzheimer's disease: an appraisal for the development of therapeutics," Nat Rev Drug Disc (September 2011), 10:698-712).

A definitive diagnosis of AD for a demented patient requires a histopathological evaluation of the number and localization of neuritic plaques and neurofibrillary tangles upon autopsy (Consensus recommendations for the post-mortem diagnosis of Alzheimer's disease. Neurobiol Aging (1997) 18: S1-2). Similar alterations are observed in patients with Trisomy 21 (Down syndrome). Plaques primarily consist of β-amyloid (Aβ) peptides that are formed by a stepwise proteolytic cleavage of the amyloid precursor protein (APP) by β-site APP-cleaving enzyme (BACE), to generate the N-terminus, and γ-secretase, to generate the C-terminus (Selkoe, D. J., Physiol Rev. (2001) 81: 741-766). γ-Secretase is a transmembrane protein complex that includes Nicastrin, Aph-1, PEN-2, and either Presenilin-1 (PS-1) or Presenilin-2 (PS-2) (Wolfe, M. S. et al., Science (2004) 305: 1119-1123). PS-1 and PS-2 are believed to contain the catalytic sites of γ-secretase.

Aβ40 is the most abundant form of Aβ synthesized (80-90%), while Aβ42 is most closely linked with AD pathogenesis. In particular, mutations in the APP, PS-1, and PS-2 genes that lead to rare, familial forms of AD implicate Aβ42 aggregates as the primary toxic species (Selkoe, D. J., Physiol Rev., (2001) 81: 741-766). Current evidence suggests that oligomeric, protofibrillar and intracellular Aβ42 play a significant role in the disease process (Cleary, J. P. et al., Nat Neurosci. (2005) 8: 79-84) Inhibitors or modulators of the enzymes that form Aβ42, such as γ-secretase, represent potential disease-modifying therapeutics for the treatment of AD.

The amyloid hypothesis suggests that a reduction in brain Aβ levels by inhibition of γ-secretase may prevent the onset and progression of AD (Selkoe, D. Physiol. Rev. (2001) 81: 741-766; Wolfe, M., J. Med. Chem. (2001) 44: 2039-2060). A large body of data continue to support the amyloid hypothesis, despite some recent failures of amyloid-targetting drugs in clinical tirals (Toyn J H, Ahlijanian M K: Interpreting Alzheimer's disease clinical trials in light of the effects on amyloid-beta. Alzheimer's Research and Therapy (2014) 6: 14). There are emerging data for the role of Aβ in other diseases, including mild cognitive impairment (MCI), Down syndrome, cerebral amyloid angiopathy (CAA), dementia with Lewy bodies (DLB), amyotrophic lateral sclerosis (ALS-D), inclusion body myositis (IBM), and age-related macular degeneration. Advantageously, compounds that inhibit or modulate γ-secretase and reduce production of Aβ or Aβ42 could be used to treat these or other Aβ-dependent diseases.

Excess production and/or reduced clearance of Aβ causes CAA (Thal, D. et al., J. Neuropath. Exp. Neuro. (2002) 61: 282-293). In these patients, vascular amyloid deposits cause degeneration of vessel walls and aneurysms that may be responsible for 10-15% of hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients. Compounds that reduce Aβ or Aβ42 levels could reduce or prevent CAA.

DLB manifests with visual hallucinations, delusions, and parkinsonism. Interestingly, familial AD mutations that cause Aβ deposits can also cause Lewy bodies and DLB symptoms (Yokota, O. et al., Acta Neuropathol (Berl) (2002) 104: 637-648). Further, sporadic DLB patients have Aβ deposits similar to those in AD (Deramecourt, V. et al., J Neuropathol Exp Neurol (2006) 65: 278-288). Based on this data, Aβ likely drives Lewy body pathology in DLB and, therefore, compounds that reduce Aβ or Ab42 levels could reduce or prevent DLB.

Approximately 25% of ALS patients have significant dementia or aphasia (Hamilton, R. L. et al., Acta Neuropathol (Berl) (2004) 107: 515-522). The majority (~60%) of these patients, designated ALS-D, contain ubiquitin-positive inclusions comprised primarily of the TDP-43 protein (Neumann, M. et al., Science (2006) 314: 130-133). About 30% of the ALS-D patients have amyloid plaques consistent with Aβ causing their dementia (Hamilton, R. L. et al., Acta Neuropathol (Berl) (2004) 107: 515-522). These patients should be identifiable with amyloid imaging agents and potentially could be treated by compounds that reduce Aβ or Aβ42 levels.

IBM is a rare, age-related degenerative disease of skeletal muscle. The appearance of Aβ deposits in IBM muscle and the recapitulation of several aspects of the disease by directing APP overexpression to muscle in transgenic mice support the role of Aβ in IBM (reviewed in Murphy, M. P. et al., Neurology (2006) 66: S65-68). Compounds that reduce Aβ or Aβ42 levels could reduce or prevent IBM.

In age-related macular degeneration, Aβ was identified as one of several components of drusen, extracellular deposits beneath the retinal pigment epithelium (RPE) (Anderson, D. H. et al., Exp Eye Res (2004) 78: 243-256). A recent study has shown potential links between Aβ and macular degeneration in mice (Yoshida, T. et al., *J Clin Invest* (2005) 115: 2793-2800). Increases in Aβ deposition and supranuclear cataracts have been found in AD patients (Goldstein, L. E. et al., *Lancet* (2003) 361: 1258-1265). Compounds that reduce Aβ or Aβ42 levels could reduce or prevent age-related macular degeneration.

Compounds which inhibit or modulate gamma secretase may also be useful in treating conditions associated with loss of myelination, for example multiple sclerosis (Watkins, T. A., et al., Neuron (2008) 60: 555-569).

A recent study by Georgetown University Medical Center researchers suggests that gamma-secretase inhibitors may prevent long-term damage from traumatic brain injury (Loane, D. J., et al., *Nature Medicine* (2009): 1-3).

A logical approach to reducing Aβ levels is to block the action of the secretases. A complementary approach is to selectively reduce production of Aβ1-42 by the action of certain compounds that serve to direct the γ-secretase-mediated cleavage of APP to instead produce shorter forms of Aβ. These shorter forms appear to aggregate less easily and solutions of the shorter forms of Aβ are less neurotoxic than solutions of Aβ1-42 (See Findeis M A: The role of amyloid β peptide 42 in Alzheimer's disease. *Pharmacol. Therapeut.* (2007) 116:266-286). Thus, compounds that selectively reduce Aβ1-42 production and their pharmaceutical compositions are beneficial agents that will prevent damage from overproduction of Aβ and are useful in treating Alzheimer's disease, Down syndrome, CAA, and inclusion body myositis, DLB, and other disorders where Aβ is overproduced.

U.S. Pat. No. 8,486,952 discloses certain compounds which are described as modulators of γ-secretase, thereby capable of reducing the production of Ab42. These compounds could be used to treat AD and possible other Aβ-dependent diseases and conditions.

What is now needed in the art are one or more additional compound(s) that are effective as γ-secretase modulators, and can reduce the production of Aβ42, and which demonstrate an acceptable safety profile and low potential for bioactivation.

SUMMARY OF THE INVENTION

In its first aspect, the present invention provides a compound, including pharmaceutically acceptable salts thereof, which is identified as N2-(3-(difluoromethoxy)-4-(3-methyl-1H-1,2,4-triazol-1-yl)phenyl)-7-(4-fluorophenyl)-N4,5,5-trimethyl-6,7-dihydro-5H-cyclopenta[d]pyrimidine-2,4-diamine as the racemate:

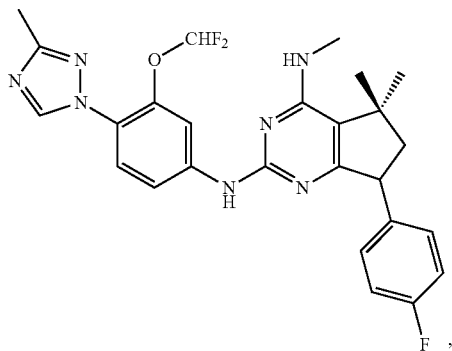

or either enantiomerically pure form, for example, the (S)-enantiomer shown below:

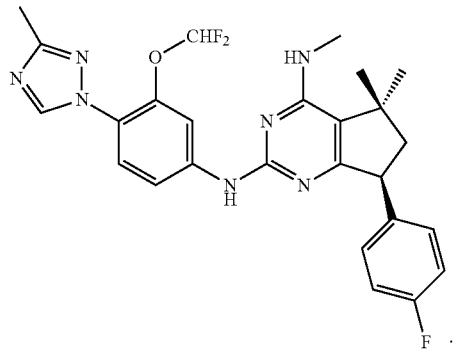

Also provided is a composition comprising the above-identified compound, including pharmaceutically acceptable salt(s) thereof, and one or more pharmaceutically acceptable carriers, diluents and/or excipients.

Further provided is a method of treating a condition, illness or disease responsive to the reduction of Aβ comprising administering a therapeutically effective amount of the above-identified compound to a patient.

The present invention is directed to these, as well as other important ends, hereinafter described.

DETAILED DESCRIPTION OF THE EMBODIMENTS

In a first aspect, the present invention provides a compound, including pharmaceutically acceptable salts thereof, which is identified as N2-(3-(difluoromethoxy)-4-(3-methyl-1H-1,2,4-triazol-1-yl)phenyl)-7-(4-fluorophenyl)-N4,5,5-trimethyl-6,7-dihydro-5H-cyclopenta[d]pyrimidine-2,4-diamine:

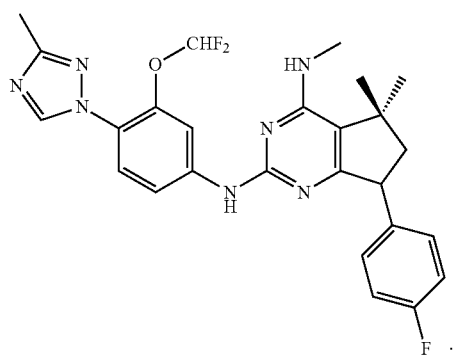

The compound is represented by its racemate, shown above, but also includes one or both of its enantiomeric forms, including the (S)-enantiomer, shown below:

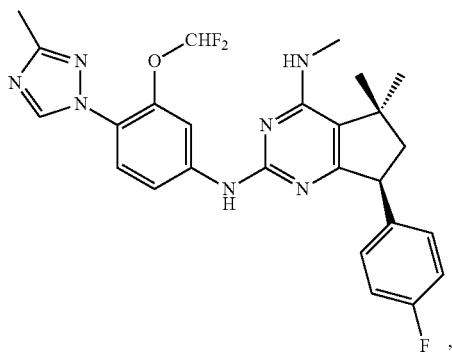

as well as the (R)-enantiomer shown below:

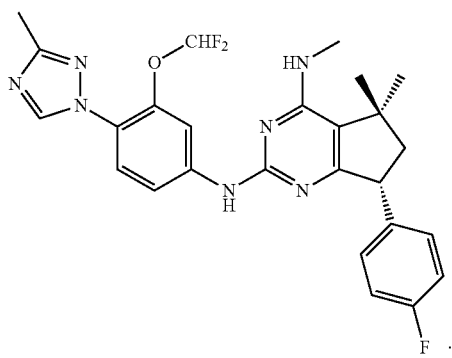

Importantly, the compound of the invention is a potent γ-secretase modulator (GSM) which lowers Aβ42 in mammals, and in addition, has low potential for bioactivation, as suggested by low CYP time-dependent inhibition, and no detectable inactivation of CYP3A4, as well as lack of GSH adducts in rat liver S9. Without being bound by any particular theory, it appears that the presence of the difluoromethoxy group and the gem-dimethyl substituents may reduce bioactivation as compared to compounds lacking the fluoro and/or gem-dimethyl substituents. These features provide the compound with a reduced in vitro bioactivation profile which may be predictive of an improved safety profile.

In a second aspect, the present invention provides a pharmaceutical composition for the treatment of disorders responsive to the reduction of β-amyloid peptide production comprising a therapeutically effective amount of the compound, including pharmaceutically acceptable salts thereof, which is identified as N2-(3-(difluoromethoxy)-4-(3-methyl-1H-1,2,4-triazol-1-yl)phenyl)-7-(4-fluorophenyl)-N4,5,5-trimethyl-6,7-dihydro-5H-cyclopenta[d]pyrimidine-2,4-diamine:

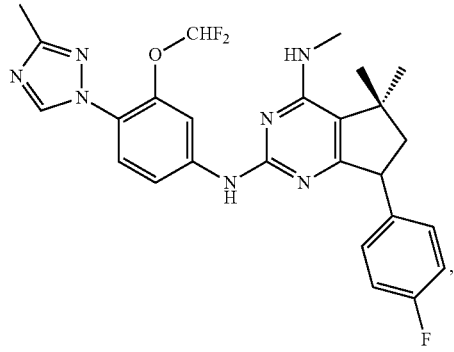

in association with one or more pharmaceutically acceptable carriers, diluents and/or excipients.

In a third aspect, the present invention provides a method for the treatment of disorders responsive to the reduction of β-amyloid peptide production in a mammal in need thereof, which comprises administering to said mammal a therapeutically effective amount of a compound, including pharmaceutically acceptable salts thereof, which is identified as N2-(3-(difluoromethoxy)-4-(3-methyl-1H-1,2,4-triazol-1-yl)phenyl)-7-(4-fluorophenyl)-N4,5,5-trimethyl-6,7-dihydro-5H-cyclopenta[d]pyrimidine-2,4-diamine:

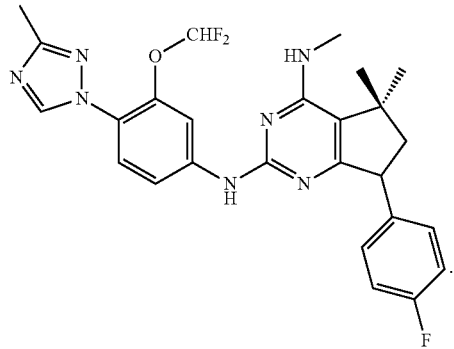

In a first embodiment of the third aspect said disorder is selected from Alzheimer's Disease (AD), Down Syndrome, mild cognitive impairment (MCI), cerebral amyloid angiopathy (CAA), dementia with Lewy bodies (DLB), amyotrophic lateral sclerosis (ALS-D), inclusion body myositis (IBM), age-related macular degeneration, and cancer.

In a second embodiment of the third aspect, said disorder is selected from Alzheimer's Disease and Down Syndrome. In a third embodiment of the third aspect, said disorder is Alzheimer's Disease.

Other aspects of the present invention may include suitable combinations of embodiments disclosed herein.

Yet other aspects and embodiments may be found in the description provided herein.

The description of the present invention herein should be construed in congruity with the laws and principals of chemical bonding. In some instances it may be necessary to remove a hydrogen atom in order to accommodate a substituent at any given location. It should be understood that the compound(s) encompassed by the present disclosure are those that are suitably stable for use as pharmaceutical agent(s).

All patents, patent applications, and literature references cited in the specification are herein incorporated by reference in their entirety. In the case of inconsistencies, the present disclosure, including definitions, will prevail.

As used herein, the singular forms "a", "an", and "the" include plural reference unless the context clearly dictates otherwise.

It should be understood that the compound of the invention encompasses all stereochemical forms, or mixtures thereof, which possess the ability to reduce β-amyloid peptide production.

The compound of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of this compound and mixtures thereof.

The present invention is intended to include all isotopes of atoms occurring in the present compound. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

The compound of the present invention may exist in zwitterionic form and the present disclosure includes each zwitterionic form of this compound and mixtures thereof.

The compound of the present invention can exist as pharmaceutically acceptable salts. The term "pharmaceutically acceptable salt," as used herein, represents salts or zwitterionic forms of the compound of the present invention which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compound or separately by reacting a suitable nitrogen atom with a suitable acid. Representative non-limiting acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compound by reacting a carboxy group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine. Other representative organic amines useful for the formation of base addition salts include ethylenediamine, ethanolamine, diethanolamine, piperidine, and piperazine.

When it is possible that, for use in therapy, therapeutically effective amounts of the compound(s) of the invention, as well as pharmaceutically acceptable salts thereof, may be administered as the raw chemical, it is possible to present the active ingredient as a pharmaceutical composition. Accordingly, the invention further provides pharmaceutical compositions, which include therapeutically effective amounts of the compound or pharmaceutically acceptable salts thereof, and one or more pharmaceutically acceptable carriers, diluents, or excipients. The compound itself and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing the compound herein set forth, or a pharmaceutically acceptable salt thereof, with one or more pharmaceutically acceptable carriers, diluents, or excipients.

The dosage of the compound to achieve a therapeutic effect will depend not only on such factors as the age, weight and sex of the patient and mode of administration, but also on the degree of Aβ42 reduction desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of the compound of the invention or pharmaceutical composition thereof for a mammal, including man, suffering from, or likely to suffer from any condition related to β-AP production as described herein, generally the daily dose will be from about 0.05 mg/kg to about 10 mg/kg and preferably, about 0.1 to 2 mg/kg when administered parenterally. For oral administration, the dose may be in the range from about 0.1 to about 75 mg/kg and preferably from 0.1 to 10 mg/kg body weight. The active ingredient will preferably be administered in equal doses from one to four times a day. However, usually a small dosage is administered, and the dosage is gradually increased until the optimal dosage for the host under treatment is determined. In accordance with good clinical practice, it is preferred to administer the instant compound at a concentration level that will produce an effective anti-amyloid effect without causing any harmful or untoward side effects. However, it will be understood that the amount of the compound actually administered will be determined by a physician, in the light of the relevant circumstances including the condition to be treated, the choice of form of compound to be administered, the chosen route of administration, the age, weight, and response of the individual patient, and the severity of the patient's symptoms.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method available in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compound of the present invention can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compound, including pharmaceutically acceptable salts thereof, which is identified as N2-(3-(difluoromethoxy)-4-(3-methyl-1H-1,2,4-triazol-1-yl)phenyl)-7-(4-fluorophenyl)-N4,5,5-trimethyl-6,7-dihydro-5H-cyclopenta[d]pyrimidine-2,4-diamine:

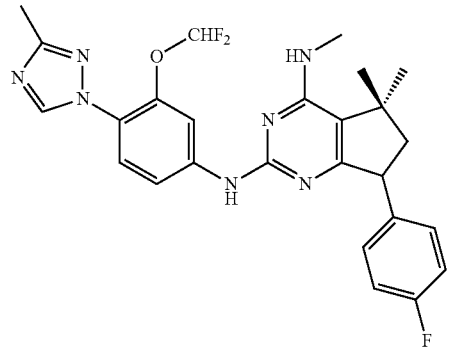

can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The above compound and pharmaceutically acceptable salts thereof may also be delivered by the use of monoclonal antibodies as individual carriers to which the compound molecules are coupled. The compound may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palitoyl residues. Furthermore, the compound may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The present invention will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present invention, it being understood that the examples are for the purposes of illustration of certain embodiments and are presented to provide what is believed to be the most useful and readily understood description of its procedures and conceptual aspects.

The compound of the present application can be synthesized using the methods described below, together with synthetic methods otherwise available in the art of synthetic organic chemistry, or variations thereon as appreciated by those skilled in the art. Preferred methods include, but are not limited to, those described below. All references cited herein are hereby incorporated in their entirety herein by reference.

The compound may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The starting materials useful to synthesize the compound(s) of the present invention are available to those skilled in the art and can be readily manufactured or are commercially available.

The following methods set forth below are provided for illustrative purposes and are not intended to limit the scope of the claims. It will be recognized that it may be necessary to prepare a compound in which a functional group is protected using a conventional protecting group, and then to remove the protecting group to provide a compound of the present invention. The details concerning the use of protecting groups in accordance with the present disclosure are available to those skilled in the art.

The abbreviations used in the present application, including particularly in the illustrative schemes and examples which follow, are well-known to those skilled in the art. For example, "EtOAc" refers to ethyl acetate, "THF" refers to tetrahydrofuran, and "DCM" refers to dichloromethane, and the like.

Methods of Preparation

Diethyl 2-(4-(4-fluorophenyl)-2-methyl-4-oxobutan-2-yl)malonate

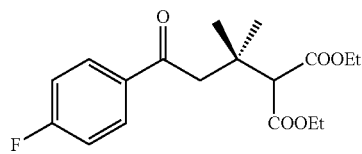

To a 0° C. cooled solution of diethyl malonate (7.19 mL, 47.1 mmol) in Ethanol (100 mL) was added sodium ethoxide (17.60 mL, 47.1 mmol) [21% Solution in ethanol] and allowed to stir for 15 min. A solution of 1-(4-fluorophenyl)-3-methylbut-2-en-1-one (7 g, 39.3 mmol) in ethanol (5 mL) was then introduced into the reaction. The resultant reaction mixture was allowed to stir for 1 h at 0° C. and 1 h at rt. The reaction mixture was then quenched with saturated ammonium chloride (50 mL) and extracted with ethyl acetate (2×150 mL). The combined organic layers were washed with water, brine, dried over sodium sulphate, filtered and concentrated under reduced pressure. The resultant crude material was then purified by using combiflash column chromatography [330 g column, 4-6% EtOAc in Hexane as eluent] to get diethyl 2-(4-(4-fluorophenyl)-2-methyl-4-oxobutan-2-yl)malonate (6.7 g, 55%) as a colorless oil.

LC/MS (M+H)+=339. 1H NMR (400 MHz, CHLOROFORM-d) δ ppm 1.20-1.32 (m, 12H), 3.28 (s, 2H), 3.89 (s, 1H), 4.12-4.25 (m, 4H), 7.11 (m, 2H), 7.96-8.02 (m, 2H).

Ethyl 4-(4-fluorophenyl)-2,2-dimethyl-5-oxocyclopentanecarboxylate

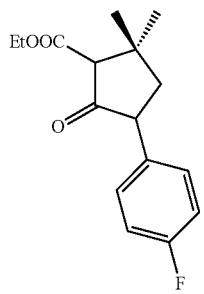

To a suspension of zinc (225 g, 3443 mmol) in THF (5000 mL) was added TiCl4 (1 M in DCM) (2754 mL, 2754 mmol) dropwise at 0° C. The mixture was heated to reflux (75° C.) for 2 h. After cooling to rt, a solution of diethyl 2-(4-(4-fluorophenyl)-2-methyl-4-oxobutan-2-yl)malonate (233 g, 689 mmol) in THF (1000 mL) was added drop wise. The resultant mixture was heated to reflux for another 3 h. After cooling the solution, 1 M HCl (2400 mL) was added and the mixture was stirred overnight. TLC (10% EtOAc/pet ether) showed complete consumption of SM and formation of new product. The reaction mixture was filtered through celite and washed with ethyl acetate (500 mL). The organic layer was separated, and the aqueous layer was extracted with ethyl acetate (3×1000 mL). Combined organics were washed with brine solution (2×500 mL), dried over sodium sulphate and concentrated under reduced pressure to give the crude material. This crude was purified by silica gel column chromatography (60-120) eluting with 1-2% EtOAc in petroleum ether to give the compound as a reddish liquid (120 g, 62% yield). 1H NMR (300 MHz, CHLOROFORM-d) δ 7.22-7.14 (m, 2H), 7.09-6.99 (m, 2H), 4.25 (qd, J=7.2, 1.1 Hz, 2H), 3.70 (dd, J=12.7, 8.5 Hz, 1H), 3.11 (s, 1H), 2.34 (dd, J=12.8, 8.3 Hz, 1H), 2.05-1.94 (m, 1H), 1.40 (s, 3H), 1.32 (t, J=7.2 Hz, 3H), 1.21 (s, 3H).

2-(3-Methyl-1H-1,2,4-triazol-1-yl)-5-nitrophenol

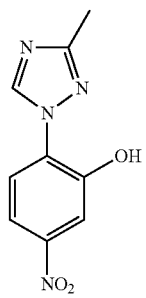 [SMILES: Cc1ncn(-c2ccc([N+](=O)[O-])cc2O)n1]

2-aminoprop-1-en-1-yl 4-methylbenzenesulfonate (0.265 g, 1.168 mmol), NMP (1.946 ml), 2-amino-5-nitrophenol (0.15 g, 0.973 mmol), triethyl orthoformate (0.178 ml, 1.071 mmol), and ethanesulfonic acid (10.72 mg, 0.097 mmol) were added to a 25 mL round-bottomed flask. The dark yellow solution was stirred at 40° C. under argon for 20 h. At that time 2-amino-5-nitrophenol had been consumed as evidenced by HPLC. The reaction mixture was diluted with water (16 mL). A thick yellow precipitate formed. The pH was adjusted to about 7 with saturated sodium bicarbonate. The suspension was stirred at rt for 1 h. The suspension was filtered and the flask and solids were washed with water (2×8 mL). The tan solid that remained was vacuum dried for 17 h. Obtained 2-(3-methyl-1H-1,2,4-triazol-1-yl)-5-nitrophenol (185.5 mg, 86% yield). LC/MS (M+H)'=221. 1H NMR (400 MHz, CHLOROFORM-d) δ ppm 11.84 (br. s., 1H), 9.14 (s, 1H), 7.98 (d, J=8.8 Hz, 1H), 7.90 (d, J=2.5 Hz, 1H), 7.88-7.82 (m, 1H), 2.41 (s, 3H).

1-(2-(Difluoromethoxy)-4-nitrophenyl)-3-methyl-1H-1,2,4-triazole

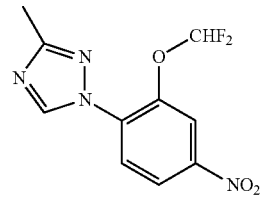

To a solution of 2-(3-methyl-1H-1,2,4-triazol-1-yl)-5-nitrophenol (5 g, 22.71 mmol), potassium carbonate (3.14 g, 22.71 mmol) in DMF (30 mL) was added ethyl chlorodifluoroacetate (3.60 g, 22.71 mmol) and heated at 70° C. for 5 h. The DMF was evaporated under high vacuum to get a dark brown solid, which was suspended in ethyl acetate (300 mL) and washed with water (2×50 mL) and brine (50 mL). The solution was dried over sodium sulphate, filtered, and evaporated under reduced pressure to provide a brown solid that was further purified by chromatography (ISCO) using 40-60% ethyl acetate as a mobile phase to give 1-((2-(difluoromethoxy)-4-nitrophenyl)-3-methyl-1H-1,2,4-triazole (10 g, 31.8 mmol, 70.1% yield) as a light brown solid. LC/MS (M+H)+=271.2 1H NMR (400 MHz, CHLOROFORM-d) δ ppm 8.74 (s, 1H) 8.23-8.27 (m, 2H), 8.15 (d, J=8.8 Hz, 1H), 6.70 (t, J=73 Hz, 1H).

3-(Difluoromethoxy)-4-(3-methyl-1H-1,2,4-triazol-1-yl)aniline

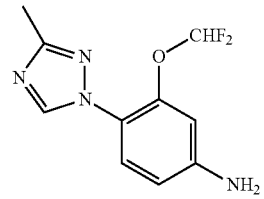 [SMILES: Cc1ncn(-c2ccc(N)cc2OC(F)F)n1]

To a nitrogen purged solution of 1-(2-(difluoromethoxy)-4-nitrophenyl)-3-methyl-1H-1,2,4-triazole (5 g, 18.51 mmol) in Methanol (150 mL) was added Pd/C (500 mg, 4.70 mmol), and the resulting mixture was stirred under hydrogen at balloon pressure for 15 hours. The reaction mixture was filtered through a bed of celite which was then washed with ethyl acetate (10 mL). The combined solution was evaporated under reduced pressure to give 3-(difluoromethoxy)-4-(3-methyl-1H-1,2,4-triazol-1-yl)aniline (4.5 g, 18.73 mmol, 101% yield) as a green solid. LC/MS (M+H)$^+$=241.0 $^1$H NMR (300 MHz, CHLOROFORM-d) δ ppm 8.26 (s, 1H), 7.40 (d, J=4 Hz, 1H), 6.24-6.61 (m, 3H), 3.96 (br, s, 2H), 2.47 (s, 3H).

1-(3-(Difluoromethoxy)-4-(3-methyl-1H-1,2,4-triazol-1-yl)phenyl)guanidine

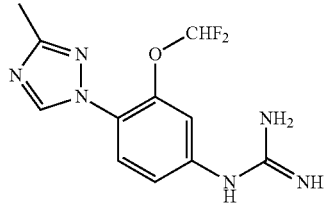 [SMILES: Cc1ncn(-c2ccc(NC(=N)N)cc2OC(F)F)n1]

To a mixture of 3-(difluoromethoxy)-4-(3-methyl-1H-1,2,4-triazol-1-yl)aniline (2.5 g, 10.41 mmol) and HCl (2.56 ml, 31.2 mmol) at 85° C. was added a hot solution (85° C.) of cyanamide (1.313 g, 31.2 mmol) in WATER (0.525 ml, 29.1 mmol). The mixture was heated for two hours. The reaction mixture was cooled to rt and water (25 mL) was added and the mixture heated at 85° C. for 15 h. The mixture was cooled to 60° C., and Na$_2$CO$_3$ (2.206 g, 20.82 mmol) in 25 mL of water was added dropwise. Stirring was continued for one h. The reaction mass was cooled to room temperature and allowed to stand for 2 h to obtain a solid compound. The mixture was filtered through a Buckner funnel and the collected solid was dried under line vacuum for 40 h to give 1-(3-(difluoromethoxy)-4-(3-methyl-1H-1,2,4-triazol-1-yl)phenyl)guanidine (1.9 g, 6.73 mmol, 64.7% yield) as a brown solid LC/MS (M+H)$^+$=283.0. $^1$H NMR (400 MHz, DMSO-d$_6$) δ ppm 8.54 (s, 1H), 7.36-7.38 (m, 2H), 6.73-6.75 (m, 2H), 5.46 (br s, 4H), 2.32 (s, 3H).

2-((3-(difluoromethoxy)-4-(3-methyl-1H-1,2,4-triazol-1-yl)phenyl)amino)-7-(4-fluorophenyl)-5,5-dimethyl-6,7-dihydro-5H-cyclopenta[d]pyrimidin-4-ol

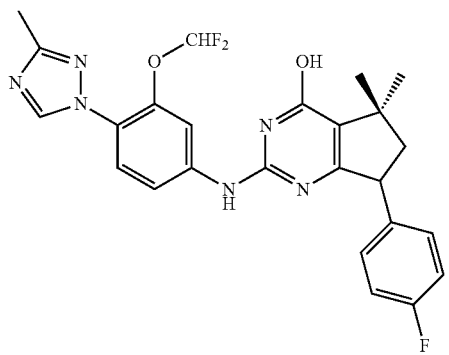

A mixture of ethyl 4-(4-fluorophenyl)-2,2-dimethyl-5-oxocyclopentanecarboxylate (1.0 g, 3.59 mmol) and 1-(3-(difluoromethoxy)-4-(3-methyl-1H-1,2,4-triazol-1-yl)phenyl)guanidine (0.507 g, 1.797 mmol) was heated at 135° C. for 1 h. The reaction mass was cooled to rt and chloroform (20 mL) was added. After stirring for 1 h, the resulting precipitate was filtered through a Buchner funnel to afford a solid which was dried under line vacuum for one hour to give 2-((3-(difluoromethoxy)-4-(3-methyl-1H-1,2,4-triazol-1-yl)phenyl)amino)-7-(4-fluorophenyl)-5,5-dimethyl-6,7-dihydro-5H-cyclopenta[d]pyrimidin-4-ol (1.0 g, 1.591 mmol, 44.3% yield) as a brown solid. LC-MS (M+H)$^+$=495.1. $^1$H NMR (400 MHz, DMSO-d$_6$) δ ppm 8.57 (s, 1H), 8.31 (s, 1H), 7.93 (br s, 1H), 7.03-7.57 (m, 7H), 6.73 (t, J=73 Hz, 1H), 4.27 (t, J=8.8 Hz, 1H), 2.29-2.37 (m, 4H), 1.78 (dd, J=9.2, 12.8 Hz, 1H), 1.44 (s, 3H), 1.29 (s, 3H).

4-Chloro-N-(3-(difluoromethoxy)-4-(3-methyl-1H-1,2,4-triazol-1-yl)phenyl)-7-(4-fluorophenyl)-5,5-dimethyl-6,7-dihydro-5H-cyclopenta[d]pyrimidin-2-amine

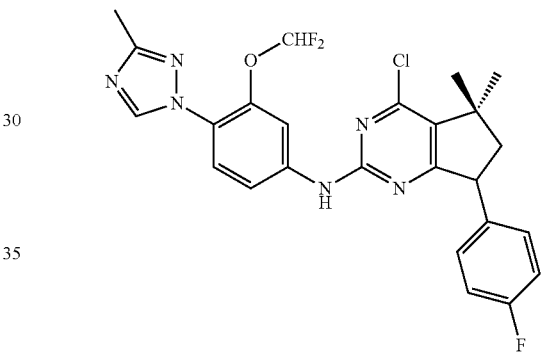

To a cooled solution of 2-((3-(difluoromethoxy)-4-(3-methyl-1H-1,2,4-triazol-1-yl)phenyl)amino)-7-(4-fluorophenyl)-5,5-dimethyl-6,7-dihydro-5H-cyclopenta[d]pyrimidin-4-ol (800 mg, 1.611 mmol) in 1,2-dichloroethane (30 mL) was added POCl$_3$ (2.103 mL, 22.56 mmol) and the mixture was heated at 80° C. for four hours. 1,2-Dichloroethane was evaporated and the crude mixture was quenched in ice (100 g) and extracted with DCM (3×150 mL). The extracts were dried over anhydrous sodium sulphate, filtered and evaporated under reduced pressure to give a light brown solid. The solid was further purified by ISCO using 2-5% of methanol in chloroform to give 4-chloro-N-(3-(difluoromethoxy)-4-(3-methyl-1H-1,2,4-triazol-1-yl)phenyl)-7-(4-fluorophenyl)-5,5-dimethyl-6,7-dihydro-5H-cyclopenta[d]pyrimidin-2-amine (450 mg, 0.856 mmol, 53.2% yield) as an off-white solid. LC/MS (M+H)$^+$=515.3. $^1$H NMR (400 MHz, CHLOROFORM-d) δ ppm 8.40 (s, 1H), 7.99 (d, J=2.4 Hz, 1H), 7.59 (d, J=8.8 Hz, 1H), 7.32 (s, 1H), 7.25-7.17 (m, 2H), 7.04-7.10 (m, 3H), 6.23 (t, J=73 Hz, 1H), 4.31 (dd, J=8.4, 10.8 Hz, 1H), 2.45-2.50 (m, 4H), 2.02 (dd, J=10.0, 13.2 Hz, 1H), 1.59 (s, 3H), 1.40 (s, 3H).

N2-(3-(Difluoromethoxy)-4-(3-methyl-1H-1,2,4-triazol-1-yl)phenyl)-7-(4-fluorophenyl)-N4,5,5-trimethyl-6,7-dihydro-5H-cyclopenta[d]pyrimidine-2,4-diamine

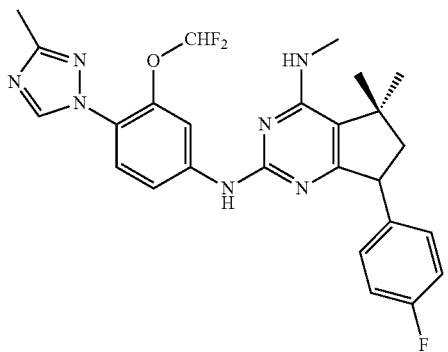

To a solution of 4-chloro-N-(3-(difluoromethoxy)-4-(3-methyl-1H-1,2,4-triazol-1-yl)phenyl)-7-(4-fluorophenyl)-5,5-dimethyl-6,7-dihydro-5H-cyclopenta[d]pyrimidin-2-amine (20 g, 38.8 mmol) in Acetonitrile (800 mL) was added DIPEA (33.9 mL, 194 mmol) and methylamine (15.08 g, 194 mmol). This mixture was allowed to stir at 60° C. for 15 h. The acetonitrile was evaporated under reduced pressure to get a residue which was further purified by flash chromatography using 40-50% of ethyl acetate in petroleum ether. The fractions having desired compound were concentrated and the component isomers were further separated by chiral normal phase HPLC [CHIRAL CEL OJH (250×20×5 micron) 1.0 mL/min of 0.2% DEA in hexane:Methanol (40:60) as mobile phase].

Enantiomer-1:

Analytical data of enantiomer (1): (79 mg, 0.149 mmol, 19.16%) of off-white solid. Chiral Retention time 1.64 min [CHIRALCEL OJH (4.6×200×5 micron) 1.0 mL/min of 0.3% DEA in Methanol:$CO_2$ (30:70) as mobile phase]. LC/MS $(M+H)^1$=510.3 $^1$H NMR (400 MHz, CHLOROFORM-d) δ ppm 1.31 (s, 3H), 1.44 (s, 3H), 1.86 (dd, J=9.6, 12.8 Hz, 1H), 2.39 (dd, J=8.4, 12.8 Hz, 1H), 2.47 (s, 3H), 3.12 (d, J=4.8 Hz, 3H), 4.18 (t, J=8.8 Hz, 1H), 4.65 (m, 1H), 6.31 (t, J=73 Hz, 1H), 6.99-7.04 (m, 3H), 7.12-7.18 (m, 3H), 7.51 (d, J=8.8 Hz, 1H), 8.24 (t, J=2.0 Hz, 1H), 8.36 (s, 1H). Isolated 6.6 g, 33% yield.

Enantiomer-2:

Analytical data of enantiomer (2): Chiral Retention time 4.4 min [CHIRALCEL OJH (4.6×200×5 micron) 1.0 mL/min of 0.3% DEA in Methanol:CO2 (30:70) as mobile phase].

Biological Methods

1. Determination of Aβ42

Aβ42 $IC_{50}$ was determined as described by Gillman, J. E. Starrett Jr., M. F. Parker, et al., "Discovery and evaluation of BMS-708163, a potent, and orally bioavailable gamma-secretase inhibitor", ACS *Medicinal Chemistry Letters*, vol. 1., pp. 120-124, 2010. Mouse brain Aβ42 was determined as described by J. H. Toyn, X-A. Lin, M. W. Thompson et al., "Viable mouse gene ablations that robustly alter bran Abeta levels are are", Biomed. Central Neuroscience, vol. 11, pp. 143, 2000.

A range of off-target receptor binding assays and enzyme assays were carried out using conventional methods available in the art.

2. Cytochrome P450 Inhibition Assays Overview

ENANTIOMER 1 was tested in two panels of assays for CYP Inhibition to determine its potential to inhibit major human Cytochrome P450 (CYP) enzymes (CYP1A2, CYP2B6, CYP2C8, CYP2C9, CYP2C19, CYP2D6, and CYP3A4). These assays were performed to determine the IC50 values, i.e. concentrations of ENANTIOMER 1 resulting in 50% inhibition of enzyme activity in incubations with CYP enzymes in the presence of reduced β-nicotinamide adenine dinucleotide phosphate (NADPH).

2.1 Inhibition of Recombinant CYP Enzymes

In one of the panels, ENANTIOMER 1 was tested using individually expressed recombinant CYP enzymes (rCYP; Supersomes™ from BD Gentest [Woburn, Mass.]), and a single IC50 value was determined in each assay, except in CYP3A4, where two IC50 values were determined after a 5- and 30-minute incubation of ENANTIOMER 1 with NADPH-fortified CYP Supersomes and probe substrates. The effect of ENANTIOMER 1 on the activity of rCYP enzymes was determined by measuring fluorescence intensity of the metabolites of the fluorogenic probe substrates in the reaction samples, and determining the IC50 values. The rCYP inhibition assays were performed as described by Vuppugalla R. et al., in *Enzyme-and Transporter-Based Drug-Drug Interactions: Progress and Future Challenges* (Pang K S, Rodrigues A D, Peter R M, eds), Springer, New York (2010) pp 585-624.

ENANTIOMER 1 was solubilized to 10 mM in 100% DMSO and then serially diluted in 100% DMSO to create a compound master plate, containing a 500× concentrated stock for a 10-point concentration response curve. Ten (10) concentrations were created by a 3-fold serial dilution of the 10 mM stock (1 part compound to 2 parts DMSO) in a 384-well polypropylene plate. The solvent (DMSO), without inhibitor, was used as control/reference for uninhibited CYP enzyme activity. Aliquots (10 nL) of the serially diluted stocks of ENANTIOMER 1 were transferred into the assay plates using noncontact acoustic liquid dispenser ECHO-550 (Labcyte Inc., Sunnyvale, Calif.).

Targeted test concentrations of ENANTIOMER 1 were 20, 6.6, 2.2, 0.74, 0.246, 0.082, 0.027, 0.009, 0.003, and 0.001 µM.

The assay conditions and concentrations of reaction components in rCYP Inhibition assays are listed in the Table 1 below.

TABLE 1

| Recombinant Cytochrome P450 Inhibition Assays: Assay Conditions | | | | | | | | |
|---|---|---|---|---|---|---|---|---|
| CYP Assay | | 1A2 | 2B6 | 2C8 | 2C9 | 2C19 | 2D6 | 3A4 |
| Probe Substrate | | CEC | EFC | DBF | MFC | CEC | AMMC | BFC |
| Probe Substrate | µM | 5 | 1.0 | 0.5 | 25 | 15 | 1.5 | 20 |
| Enzyme | nM | 1.1 | 13.5 | 7.5 | 12.5 | 7.3 | 6.3 | 4.0 |

TABLE 1-continued

Recombinant Cytochrome P450 Inhibition Assays: Assay Conditions

| | | | | | | | | |
|---|---|---|---|---|---|---|---|---|
| KPi Buffer | mM | 100 | 100 | 50 | 25 | 50 | 100 | 200 |
| NADP | mM | 1.3 | 1.3 | 1.3 | 1.3 | 1.3 | 0.008 | 1.3 |
| Incubation Time | min | 45 | 20 | 20 | 60 | 45 | 45 | 5 and 30 |
| Excitation/Emission/ | nm | 405/460 | 425/535 | 485/535 | 425/535 | 405/460 | 405/460 | 425/535 |
| Cut-off filter wavelength | | 430 | 505 | 505 | 505 | 430 | 430 | 505 |

KPi = potassium phosphate buffer, pH 7.4;
NADP = nicotinamide adenine dinucleotide phosphate;
Substrate probes: 3-cyano-7-ethoxy-coumarin (CEC), 7-ethoxy-4-trifluoromethyl-coumarin (EFC), dibenzyl-fluorescein (DBF), 7-methoxy-4-trifluoromethyl-coumarin (MFC), 3-[2-(N,N-diethyl-N-methylamino)ethyl]-7-methoxy-4-methyl-coumarin (AMMC), 7-benzyloxy-4-trifluoromethyl-coumarin (BFC), purchased from BD Gentest (Woburn, MA).
In all assays, test concentrations of ENANTIOMER 1 were 1 nM-20 µM, and DMSO concentration in reaction mixtures was 0.2%.

2.2 Recombinant CYP Inhibition Assay Results for ENANTIOMER 1

The $IC_{50}$ values obtained for ENANTIOMER 1 in the rCYP and HLM CYP Inhibition panels are provided in

TABLE 2

(a) Inhibition of rCYP Enzymes by ENANTIOMER 1 ($IC_{50}$, µM):
ENANTIOMER 1 was tested in the rCYP Inhibition assays in two independent experiments, in duplicate in each experiment. The average $IC_{50}$ values are shown.

| CYP Enzyme | 1A2 | 2B6 | 2C8 | 2C9 | 2C19 | 2D6 | 3A4-(5 min) | 3A4-(30 min) |
|---|---|---|---|---|---|---|---|---|
| rCYP IC50 | >20 | >20 | 0.96 | 1.3 | 0.96 | >20 | 1.45 | 1.45 |

(b) Inhibition of CYP Enzymes by ENANTIOMER 1 in Human Liver Microsomes ($IC_{50}$, µM): ENANTIOMER 1 was tested in the HLM CYP Inhibition assays in a single experiment as n = 1, except for CYP3A4 assays (with midazolam and testosterone), in which it was tested in two independent experiments. The average IC50 values are shown for the CYP3A4 assays.

| CYP Enzyme | 1A2 | 2B6 | 2C8 | 2C9 | 2C19 | 2D6 | 3A4-(MDZ) | 3A4-(TST) |
|---|---|---|---|---|---|---|---|---|
| IC50-0 min | >40 | >40 | 4.2 | 12.7 | 22.6 | 34.5 | ~40 | 12.0 |
| IC50-30 min | >40 | >40 | 2.2 | 8.8 | 12.2 | 15.6 | 15.1 | 4.5 |
| IC50 Ratio | 1.0 | 1.0 | 1.9 | 1.4 | 1.9 | 2.2 | 2.6 | 2.7 |

MDZ = midazolam; TST = testosterone.

2.3 Inhibition of CYP Enzymes in HLM

In the other panel, ENANTIOMER 1 was tested using human liver microsomes (HLM, pooled from 150 individual donors) as the source of CYP enzymes (from BD Gentest [Woburn, Mass.]) and FDA-recommended probe substrates that produce enzyme-specific metabolites. Each assay in this panel was performed to determine both reversible and time-dependent $IC_{50}$ values for ENANTIOMER 1 and assess the $IC_{50}$ shift after a 30-minute preincubation of ENANTIOMER 1 with NADPH-fortified HLM.

ENANTIOMER 1 (0.002 to 40 µM) was preincubated with NADPH-fortified HLM at 37° C. for 0 and 30 minutes, followed by addition of a CYP-specific probe substrate and an additional incubation at 37° C. At the end of the incubation, reactions were terminated by adding quench buffer containing reaction-specific internal standard. Cytochrome P450 enzyme activities were determined by quantification of a CYP-specific metabolite of the probe substrate using solid-phase extraction followed by tandem mass spectrometry (SPE-MS/MS), or by LC-MS/MS analysis. The results were expressed as percent inhibition of cytochrome P450 activities and the concentrations of inhibitors that result in 50% inhibition (IC50 values) of CYP enzyme activity were determined. CYP inhibition assays in HLM were performed as described by Zvyaga T. et al., *Drug Metab Dispos* (2012) 40: 1698-1711, except for midazolam concentration in CYP3A4-Midazolam assay, which was 2.5 µM in this study.

ENANTIOMER 1 was solubilized to 20 mM in 100% DMSO and then serially diluted in 100% DMSO to create a compound master plate, containing a 500× concentrated stock for a 10-point concentration response curve. Ten (10) concentrations were created by a 3-fold serial dilution of the 20 mM stock (1 part compound to 2 parts DMSO) in a 384-well polypropylene plate. The solvent (DMSO), without inhibitor, was used as control/reference for uninhibited CYP enzyme activity. Aliquots (20 nL) of the serially diluted stocks of ENANTIOMER 1 were transferred into the assay plates using noncontact acoustic liquid dispenser ECHO-550 (Labcyte Inc., Sunnyvale, Calif.).

Targeted test concentrations of ENANTIOMER 1 were 40, 13.3, 4.4, 1.48, 0.494, 0.165, 0.055, 0.018, 0.006, and 0.002 µM.

The effects of ENANTIOMER 1 and positive controls on the rate of phenacetin 0-deethylation (CYP1A2 activity), bupropion hydroxylation (CYP2B6 activity), amodiaquine N-deethylation (CYP2C8 activity), diclofenac 4'-hydroxylation (CYP2C9 activity), (S)-mephenytoin 4'-hydroxylation (CYP2C19 activity), dextromethorphan 0-demethylation (CYP2D6 activity), midazolam 1'-hydroxylation (CYP3A4 activity), and testosterone 6β-hydroxylation (CYP3A4 activity) were evaluated as previously described (Zvyaga T. et al., *Drug Metab Dispos* (2012) 40: 1698-1711).

In both panels, 12 known CYP inhibitors (reversible and time-dependent/mechanism-based) were tested alongside ENANTIOMER 1 as positive controls in each experiment. The $IC_{50}$ values for positive controls were within their respective historical ranges (Table 3); thus, the assay data were accepted for evaluation of the ENANTIOMER 1 potential to inhibit major cytochrome P450 enzymes.

TABLE 3

Inhibition of Cytochrome P450 Enzymes in Human Liver Microsomes
Assay: Historical Values for Positive Controls

| Enzyme | Control | IC$_{50}$ Value (µM) | | | |
|---|---|---|---|---|---|
| | | No Preincubation | | 30-min Preincubation | |
| | | Mean | Range | Mean | Range |
| CYP1A2 | Furafylline | >10 | >10 | 0.520 | 0.350-0.850 |
| | Fluvoxamine | 0.870 | 0.600-1.20 | 0.044 | 0.020-0.090 |
| CYP2B6 | Ticlopidine | 0.089 | 0.055-0.140 | 0.030 | 0.020-0.050 |
| | Clotrimazole | 0.140 | 0.080-0.20 | 0.370 | 0.280-0.570 |
| | Paroxetine | 1.35 | 0.800-2.20 | 1.75 | 1.00-3.50 |
| CYP2C8 | Montelukast | 0.053 | 0.030-0.085 | 0.036 | 0.020-0.060 |
| | Clotrimazole | 0.780 | 0.500-1.10 | 0.840 | 0.520-1.20 |
| CYP2C9 | Sulfa-phenazole | 0.340 | 0.250-0.500 | 0.340 | 0.250-0.500 |
| | Tienilic Acid | 0.530 | 0.330-0.700 | 0.056 | 0.033-0.080 |
| CYP2C19 | Fluvoxamine | 0.400 | 0.230-0.550 | 0.430 | 0.250-0.600 |
| | Ticlopidine | 0.860 | 0.670-1.10 | 0.540 | 0.420-0.700 |
| CYP2D6 | Quinidine | 0.100 | 0.070-0.140 | 0.060 | 0.035-0.080 |
| | Paroxetine | 1.06 | 0.700-1.50 | 0.073 | 0.050-0.110 |
| | Mibefradil | 1.32 | 1.00-1.70 | 0.440 | 0.300-0.550 |
| CYP3A4 (MDZ) | Ketoconazole | 0.024 | 0.016-0.035 | 0.025 | 0.016-0.035 |
| | Clotrimazole | 0.009 | 0.006-0.012 | 0.011 | 0.005-0.017 |
| | Mibefradil | 0.920 | 0.550-1.30 | 0.041 | 0.020-0.062 |
| | Verapamil | 32.3 | 20.0-55.0 | 4.2 | 2.00-6.40 |
| CYP3A4 (TST) | Ketoconazole | 0.035 | 0.020-0.050 | 0.021 | 0.012-0.035 |
| | Clotrimazole | 0.017 | 0.010-0.023 | 0.007 | 0.005-0.009 |
| | Mibefradil | 1.66 | 1.00-2.400 | 0.022 | 0.018-0.029 |
| | Verapamil | 30.0 | 20.0-41.0 | 2.10 | 1.20-4.20 |

3. Cytochrome P450 Inactivation Assays
3.1 Overview

Since ENANTIOMER 1 demonstrated time-dependent inhibition of CYP3A4 enzyme in HLM, it was further tested in the HLM CYP3A4 Inactivation Assay to determine whether or not ENANTIOMER 1 is a mechanism-based inhibitor of CYP3A4, i.e., evaluate its ability to inactivate the CYP3A4 enzyme in human liver microsomes (HLM) and determine kinetic parameters of CYP3A4 inactivation: the maximal inactivation rate ($k_{inact}$) and concentration of ENANTIOMER 1 corresponding to the half-maximal rate of inactivation ($K_I$).

Assay and data analysis methodology principles used in this study were as described by Ghanbari F. et al., (2006) *Current Drug Metab,* 7:315-334. Human liver microsomes pooled from 150 donors (UltraPool 150), [$^{13}C_3$]1'-hydroxymidazolam and [$^2H_7$]6β-hydroxytestosterone were purchased from BD Gentest (Woburn, Mass.), midazolam and testosterone from Sigma-Aldrich (Saint Louis, Mo.), NADPH from AKRON Biotech (Boca Raton, Fla.).

3.2 Experimental Procedure

ENANTIOMER 1 (0.31 to 20 µM) was preincubated with HLM (1 mg/mL, 100 µL) in the presence of reduced β-nicotinamide adenine dinucleotide phosphate (NADPH) for 0, 5, 10, 15, 20, and 25 minutes at 37° C. At each time point, the remaining CYP3A4 activity was assessed by diluting (10-fold) the reaction samples (10 µL) in the secondary reaction mixture (90 µL) containing probe substrate (midazolam [50 µM, ~20×Km] or testosterone [330 µM, ~6×Km]). After a 2-minute incubation at 37° C., the secondary reactions were terminated by the addition of a quench buffer (1:1, v/v), containing an internal standard (stable-isotope-labeled metabolite of the probe substrate). Verapamil, a known time-dependent/mechanism-based CYP3A4 inhibitor, was tested alongside ENANTIOMER 1 as a positive control in each experiment.

ENANTIOMER 1 and verapamil were solubilized to 20 mM in 100% DMSO, and then diluted 10-fold in acetonitrile, resulting in a 2 mM stock solution, which was then serially diluted in a mixture of acetonitrile and DMSO (9:1, v/v). Seven (7) test concentrations of ENANTIOMER 1 and verapamil were created by a 2-fold serial dilution of the 2 mM stock (1 part compound to 1 parts acetonitrile-DMSO mixture), and were used as 100× stocks that were added (1 µL) to the primary reaction mixtures (100 µL) containing HLM. Targeted test concentrations of ENANTIOMER 1 and verapamil were 20, 10, 5, 2.5, 1.25, 0.625, and 0.312 µM. The solvent (acetonitrile: DMSO, 9:1, v/v) without inhibitor was used as control/reference for uninhibited CYP3A4 activity.

Reaction buffer (in both primary and secondary reactions) consisted of 100 mM potassium phosphate, pH 7.4, 2 mM MgCl$_2$, and 1 mM NADPH. Quench buffer was a mixture of water, acetonitrile, and formic acid (94:5:1, v/v/v) containing one of the internal standards (0.2 µM [$^{13}C_3$]1'-hydroxymidazolam or 3 µM [$^2H_7$]6β-hydroxytestosterone).

Quenched reaction mixtures (in 96-well microplates) were initially frozen at −80° C. and then, before LC-MS/MS analysis, the samples were thawed at room temperature and centrifuged at ~2500×g for 10 minutes to precipitate denatured microsomal protein. Supernatants were used to quantify the amount of a metabolite of the probe substrate in the reaction samples.

The effects of ENANTIOMER 1 and verapamil on the rate of midazolam 1'-hydroxylation or testosterone 6β-hydroxylation (CYP3A4 activity) at each time point and each inhibitor concentration were evaluated by quantification of a metabolite of the probe substrate in the reaction samples using liquid chromatography followed by tandem mass spectrometry (LC-MS/MS) analysis.

3.3 LC-MS/MS Analysis of Assay Samples

The LC-MS/MS system consisted of a Thermo Cohesive ARIA LX-2 (Waltham, Mass.) with Shimadzu LC-20AD XR pumps (Kyoto, Japan) for gradient elution and an AB Sciex API 4500 triple-quadrupole mass spectrometer (Foster City, Calif.), using Turbo V™ source for sample analysis. Samples were injected using dual-arm CTC HTS PAL autosampler from LEAP Technologies (Carrboro, N.C.

To quantify 1'-hydroxymidazolam, the mass spectrometer was operated under positive ionization mode and SRM used for analysis. The SRM transitions were 342.1→203.1 and 345.1→206.1 for 1'-hydroxymidazolam and the internal standard ([$^{13}C_3$]1'-hydroxymidazolam), respectively. The dwell time was 75 ms for each transition. The declustering potential was 70 V and the collision energy 38 eV. A Kinetex 2.6 µm XB-C18 100A, 50 mm×2.1 mm HPLC column from Phenomenex (Torrance, Calif.) and the injection volume was 10 µL. Mobile phase A was water with 0.2% formic acid, and mobile phase B was acetonitrile with 0.2% formic acid. The flow rate was 0.9 mL/min for both mobile phases A and B. The LC method was as follows: 5 second hold at 98% A/2% B, 40 second ramp from 98% A/2% B to 2% A/98% B, step to 100% B for 20 seconds, and finally step to 98% A/2% B for 25 seconds. The total cycle time was 90 seconds per injection.

To quantify 6β-hydroxytestosterone, the mass spectrometer was operated under positive ionization mode and SRM used for analysis. The SRM transitions were 305.2→269.2 and 312.2→276.2 for 6β-hydroxytestosterone and the internal standard ([$^2H_7$]6β-hydroxytestosterone), respectively. The dwell time was 75 ms for each transition. The declustering potential was 75 V and the collision energy 21.5 eV. A Kinetex 2.6 µm XB-C18 100A, 50 mm×2.1 mm HPLC column from Phenomenex (Torrance, Calif.) was used for analysis and the injection volume was 10 µL. Mobile phase A was water with 0.2% formic acid, and mobile phase B was acetonitrile with 0.2% formic acid. The LC method is as follows: 5 second hold at 98% A/2% B, 40 second ramp from 98% A/2% B to 2% A/98% B, step to 100% B for 20 seconds, and finally step to 98% A/2% B for 25 seconds. The total cycle time was 90 seconds per injection.

The data acquired for CYP3A4-Midazolam and CYP3A4-Testosterone assays were processed using Analyst 1.6.1 software (AB Sciex). Processed data were exported to an Excel file, which was used for data analysis and determination of kinetic parameters of inactivation.

3.4 Data Analysis and Results

The signal intensity of the metabolite in MS/MS analysis was normalized to the signal of internal standard; thus signal intensity was expressed as signal ratio. Each sample signal ratio was then normalized to signal ratios of the reactions performed in the absence of the test substance (solvent control, 100% activity). Thus, the results for each pair of inhibitor concentration and time point were expressed as percent of the CYP3A4 activity remaining after preincubation as compared to the enzyme activity observed in the absence of inhibitor (solvent control). Percent CYP3A4 enzyme activity remaining after preincubation was calculated as:

% Activity(Remaining)=(S/T)*100

Where: S=sample signal, T=solvent control signal,

An apparent rate of inactivation ($k_{obs}$) observed at a given inhibitor concentration was estimated from the initial slope of a plot of the natural log of enzyme activity remaining after preincubation against preincubation time (corrected for any loss of activity in the absence of inhibitor). The kinetic parameters ($k_{inact}$ and $K_I$) were then calculated by fitting the $k_{obs}$ values plotted against inhibitor concentrations ([I]) using the non-linear regression model (Michaelis-Menten equation) in the GRAPH PAD PRISM v.5.0 software (San Diego, Calif.):

$$Kobs = \frac{Kinact \times [I]}{KI + [I]}$$

Where: [I]=inhibitor concentration; $k_{inact}$=maximal inactivation rate;

$K_1$=inhibitor concentration corresponding to half-maximal rate of inactivation;

$k_{obs}$=apparent rate of inactivation observed at a given inhibitor concentration.

When $k_{obs}$ values at majority of tested concentrations are below 0.005 (or even 0.010), the apparent inactivation rates are considered too low to accurately measure, i.e. loss of enzyme activity over time is minimal (or not detectable) and it does not consistently increase as the inhibitor concentrations increase. Therefore, the kinetic parameters of inactivation ($k_{inact}$ and $K_I$) cannot be determined in such cases.

Assay Results

ENANTIOMER 1 was tested in CYP3A4 Inactivation assays to determine whether or not it is a mechanism-based CYP3A4 inhibitor. ENANTIOMER 1 was tested in each assay at 7 concentrations in duplicate.

The above tests, CYP3A4 Inactivation assays with midazolam and with testosterone as probe substrates, demonstrated that ENANTIOMER 1 did not cause any significant (reliably measurable) loss of CYP3A4 activity in HLM over time (up to 25 min) at any of the tested concentrations (0.31-20 µM), i.e. apparent rates of inactivation ($k_{obs}$) at all tested concentrations were too low (<0.003 with midazolam, <0.006 with testosterone) and did not show any consistent trend of increasing at higher test concentrations of ENANTIOMER 1. Therefore, the kinetic parameters of inactivation, $k_{inact}$ and $K_I$ values, could not be determined for ENANTIOMER 1.

Verapamil, a known mechanism-based inhibitor of CYP3A4, tested in this study alongside ENANTIOMER 1 as a positive control, demonstrated significant loss of CYP3A4 activity over time in a concentration-dependent manner. The kinetic parameters of CYP3A4 inactivation by verapamil were consistent with those historically observed in this assay: in CYP3A4-midazolam assay $k_{inact}$ value was 0.0473±0.0043 (min$^{-1}$) and $K_I$ value was 5.7±0.3 (µM), n=2; in CYP3A4-testosterone assay $k_{inact}$ value was 0.0473±0.0008 (min$^{-1}$) and $K_I$ value was 4.9±0.3 (µM), n=2.

These results suggest that ENANTIOMER 1 is not a mechanism-based inhibitor of CYP3A4.

Biotransformation Methods

1. In Vitro Metabolite Elucidation in Aroclor-Treated Rat Liver S9

The incubation mixtures (0.5 mL) contained N2-(3-(DI-FLUOROMETHOXY)-4-(3-METHYL-1H-1,2,4-TRI-AZOL-1-YL)PHENYL)-7-(4-FLUOROPHENYL)-N4,5,5-TRIMETHYL-6,7-DIHYDRO-5H-CYCLOPENTA[D]PYRIMIDINE-2,4-DIAMINE (10 µM), liver S9 fractions from Aroclor 1254-treated rats (Molecular Toxicology, Boone, N.C.) (2 mg protein/mL), and glutathione (GSH, 5 mM) in a 100 mM potassium phosphate buffer (pH 7.4). The final concentration of acetonitrile in the S9 fraction incubations was 0.5% (v/v). The reactions were initiated by adding β-nicotinamide adenine dinucleotide 2'-phosphate reduced tetrasodium salt (NADPH, final concentration as 1 mM) and the incubations were carried out at 37° C. At 0 and 30 minutes, aliquots (150 µL) were collected and reactions were terminated by adding 3 volumes of acetonitrile. Protein was removed using a Strata Protein Precipitation Plate (Phenomenex, Torrance, Calif.) and centrifugation at 1500×g for 2 minutes. The filtrate was collected in a 96-well plate and evaporated to approximately 25% of the original volume under nitrogen gas, and the remaining aqueous phase was analyzed using high-performance liquid chromatography with ultraviolet (UV) spectroscopic and mass spectrometric detection (LC-UV/MS) under the conditions described in Section 1.2.

Bioanalytical methods were as follows: The LC-UV/MS system consisted of a Waters Acquity binary solvent manager, a sample manager, a photodiode array (PDA) detector, and a Xevo Q-TOF mass spectrometer (Waters Corporation, Milford, Mass.). Chromatographic separations employed a Waters BEH C18 column (1.7 µm, 2.1×100 mm) using mobile phase A [water/acetonitrile/formic acid, 95/5/0.1 (v/v/v)] and mobile phase B (100% acetonitrile) with a linear gradient delivered at 0.3 mL/min as follows: 5% B isocratic for 1 min, 5% to 35% B over 5.5 min, 35% to 100% B over 3.5 min, and 100% B isocratic for 1 min. The gradient was then returned to initial conditions, and the column was rebalanced for 1.5 min. The HPLC elution gradient is shown in Table 1. The sample injection volume was 5 µL. Column effluent was analyzed in-line using a PDA detector followed by the mass spectrometer. Ultraviolet absorbance of drug-related materials was scanned across the range of 200-400 nm (5 Hz) with designated monitoring at 300 nm. The mass spectrometer was equipped with an electrospray ionization source and operated in the positive-ion mode. To obtain the maximum sensitivity (based on the parent molecule), the source temperature was 125° C., the desolvation temperature was 250° C., capillary voltage was 3 kV, sampling cone was 30 (arbitrary units) and extraction cone was 1.7 (arbitrary units). All mass spectrometry data were acquired at a low collision voltage (5 V) and a high voltage ramp (25-40 V), and post-acquisition analysis was conducted using Metabolynx software (Waters Corp).

2. Biotransformation Results

Multiple metabolites of N2-(3-(DIFLUOROMETHOXY)-4-(3-METHYL-1H-1,2,4-TRIAZOL-1-YL)PHENYL)-7-(4-FLUOROPHENYL)-N4,5,5-TRIMETHYL-6,7-DIHYDRO-5H-CYCLOPENTA[D]PYRIMIDINE-2,4-DIAMINE (Enantiomer 1) were identified. The relative abundances of N2-(3-(DIFLUOROMETHOXY)-4-(3-METHYL-1H-1,2,4-TRIAZOL-1-YL)PHENYL)-7-(4-FLUOROPHENYL)-N4,5,5-TRIMETHYL-6,7-DIHYDRO-5H-CYCLOPENTA[D]PYRIMIDINE-2,4-DIAMINE and its metabolites (see Table 2) were estimated by comparing the HPLC/UV peak areas at 300 nm that corresponded to these compounds in each sample, employing the assumption that the molar extinction coefficients of N2-(3-(DIFLUOROMETHOXY)-4-(3-METHYL-1H-1,2,4-TRIAZOL-1-YL)PHENYL)-7-(4-FLUOROPHENYL)-N4,5,5-TRIMETHYL-6,7-DIHYDRO-5H-CYCLOPENTA[D]PYRIMIDINE-2,4-DIAMINE (Enantiomer 1) and its metabolites were equal. Metabolite structures were assigned based on their positive-ion electrospray LC-MS/MS product-ion mass spectra. The proposed metabolite structures are shown in the following scheme.

Key routes of biotransformation of N2-(3-(DIFLUOROMETHOXY)-4-(3-METHYL-1H-1,2,4-TRIAZOL-1-YL)PHENYL)-7-(4-FLUOROPHENYL)-N4,5,5-TRIMETHYL-6,7-DIHYDRO-5H-CYCLOPENTA[D]PYRIMIDINE-2,4-DIAMINE (Enantiomer 1) included:

Mono-hydroxylation of the dimethylcyclopentyl or N-methyl, yielding Met6, Met8, Met9 and Met11
Bis-hydroxylation of the dimethylcyclopentyl or N-methyl, yielding Met5
Bis-hydroxylation of the dimethylcyclopentyl or N-methyl and desaturation, yielding Met4
Desaturation of the dimethylcyclopentyl, yielding Met12
O-Dedifluoromethylation, yielding Met7
Bis-hydroxylation, yielding Men and Met2
Mono-hydroxylation, yielding Met3 and Met9

2.1 In Vitro Biotransformation

The biotransformation of N2-(3-(DIFLUOROMETHOXY)-4-(3-METHYL-1H-1,2,4-TRIAZOL-1-YL)PHENYL)-7-(4-FLUOROPHENYL)-N4,5,5-TRIMETHYL-6,7-DIHYDRO-5H-CYCLOPENTA[D]PYRIMIDINE-2,4-DIAMINE (Enantiomer 1) was studied using liver S9 fractions from Aroclor-treated rats, and the result is summarized in Table 2.

After 30-minute incubations supplemented with NADPH and GSH, 76% of Enantiomer 1 (10 μM) remained. The main metabolic pathways that were active against N2-(3-(DIFLUOROMETHOXY)-4-(3-METHYL-1H-1,2,4-TRIAZOL-1-YL)PHENYL)-7-(4-FLUOROPHENYL)-N4,5,5-TRIMETHYL-6,7-DIHYDRO-5H-CYCLOPENTA[D]PYRIMIDINE-2,4-DIAMINE (Enantiomer 1) were oxidation on the dimethylcyclopentyl and/or N-methyl moieties, forming multiple mono-hydroxylation products (Met6, Met8, Met9, and Met11), one bis-hydroxylation product (Met5), one desaturation product (Met12) and one bis-hydroxylation and desaturation product (Met4). O-Dedifluoromethylation represented a minor pathway, yielding Met7. In addition, there were products formed via mono-hydroxylation (yielding Men and Met2) and via bis-hydroxylation (Met3 and Met9) on unidentified sites. No GSH conjugates were detected.

TABLE 4

| In vitro Biotransformation results | | | | | | | | | | | | | |
|---|---|---|---|---|---|---|---|---|---|---|---|---|---|
| Estimated Percent (%) of The Original Parent Level (P) Based on UV Peak Areas | | | | | | | | | | | | | |
| | P | Met1 | Met2 | Met3 | Met4 | Met5 | Met6 | Met7 | Met8 | Met9 | Met10 | Met11 | Met12 |
| % | 76 | 2 | <1 | <1 | 4 | 1 | 11 | ms | 1 | 1 | 1 | 2 | <1 |

Additional information: ms, detected only by mass spectrometry

Further Compound Measurements for N2-(3-(difluoromethoxy)-4-(3-methyl-1H-1,2,4-triazol-1-yl)phenyl)-7-(4-fluorophenyl)-N4,5,5-trimethyl-6,7-dihydro-5H-cyclopenta[d]pyrimidine-2,4-diamine (Enantiomer 1), including $IC_{50}$:

| | |
|---|---|
| Aβ42 $IC_{50}$ | 1.2 + 0.5 nM |
| Mouse Aβ42 | 29/68% @ 1334/391 nM; 30/8 mpk; B/P = 1.4/0.7 |
| rCYP3A4 $IC_{50}$ | 1.45 μM; TDI ratio = 1.0 |
| HLM 3A4 $IC_{50}$ | with MDZ: ~40 μM; TDI ratio = 2.6 |
| | with TST: ~12 μM; TDI = 2.7 |

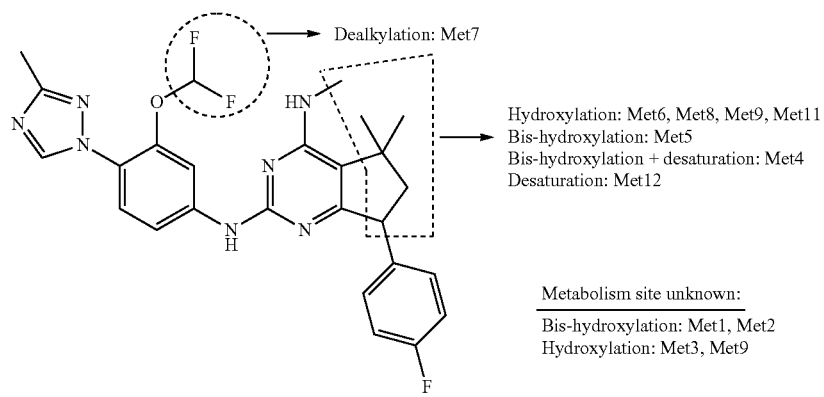

Dealkylation: Met7

Hydroxylation: Met6, Met8, Met9, Met11
Bis-hydroxylation: Met5
Bis-hydroxylation + desaturation: Met4
Desaturation: Met12

Metabolism site unknown:
Bis-hydroxylation: Met1, Met2
Hydroxylation: Met3, Met9

-continued

| | |
|---|---|
| GSH Adducts | Not detected in Aroclor-treated rat liver S9; KCN trapping & BDC study not performed |
| HLM TDI panel | 3A4 TDI ratio = 2.7, 2D6 = 2.2; others <2 |
| KI; Kinact | Inactivation rates below the limit of reliable detection |
| In vitro safety: | |
| 43 receptor and Enzyme IC$_{50}$s (µM) | A2A = 2; DAT, D1 MAO A = 8-10; all others >10 |

A2A = adenosine 2A receptor; DAT = dopamine transporter; D1 = dopamine receptor 1; MAO A = monoamine oxidase A.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, and all changes which come within the meaning and range of equivalency of the claims are therefore intended to be embraced therein.

What is claimed is:

1. A compound, including pharmaceutically acceptable salts thereof, which is N2-(3-(difluoromethoxy)-4-(3-methyl-1H-1,2,4-triazol-1-yl)phenyl)-7-(4-fluorophenyl)-N4,5,5-trimethyl-6,7-dihydro-5H-cyclopenta[d]pyrimidine-2,4-diamine:

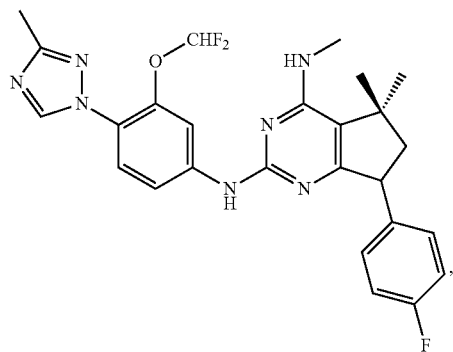

said compound including the racemate and its enantiomers.

2. The compound as claimed in claim 1, which is the enantiomeric form of the compound as shown structurally below:

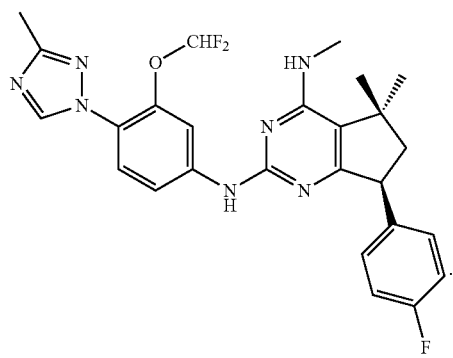

3. The compound as claimed in claim 1, which is the enantiomeric form of the compound as shown structurally below:

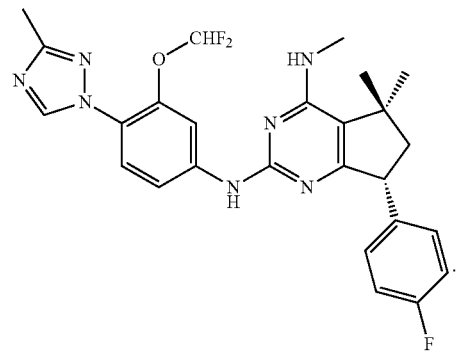

4. A pharmaceutical composition for the treatment of disorders responsive to the reduction of β-amyloid peptide production comprising a therapeutically effective amount of a compound of claim 1, or a pharmaceutically acceptable salt thereof, in association with a pharmaceutically acceptable carrier, excipient or diluent.

5. A pharmaceutical composition for the treatment of disorders responsive to the reduction of β-amyloid peptide production comprising a therapeutically effective amount of a compound of claim 2, or a pharmaceutically acceptable salt thereof, in association with a pharmaceutically acceptable carrier, excipient or diluent.

6. A compound, including pharmaceutically acceptable salts thereof, which is N2-(3-(difluoromethoxy)-4-(3-methyl-1H-1,2,4-triazol-1-yl)phenyl)-7-(4-fluorophenyl)-N4,5,5-trimethyl-6,7-dihydro-5H-cyclopenta[d]pyrimidine-2,4-diamine, which is identified as Enantiomer 1.

7. A compound, including pharmaceutically acceptable salts thereof, which is N2-(3-(difluoromethoxy)-4-(3-methyl-1H-1,2,4-triazol-1-yl)phenyl)-7-(4-fluorophenyl)-N4,5,5-trimethyl-6,7-dihydro-5H-cyclopenta[d]pyrimidine-2,4-diamine, which is identified as Enantiomer 2.

* * * * *